(12) United States Patent
Yasuda et al.

(10) Patent No.: US 8,633,433 B2
(45) Date of Patent: Jan. 21, 2014

(54) OPTICAL POTENTIOMETER HAVING AN OPTICAL ELEMENT WITH OPTICAL PROPERTY CONTINUOUSLY VARYING ALONG A MOVING DIRECTION AND OPERATING DEVICE

(71) Applicant: Olympus Corporation, Tokyo (JP)

(72) Inventors: Mamoru Yasuda, Hino (JP); Takahiro Komuro, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 13/662,438

(22) Filed: Oct. 27, 2012

(65) Prior Publication Data

US 2013/0050713 A1 Feb. 28, 2013

Related U.S. Application Data

(63) Continuation of application No. PCT/JP2011/056259, filed on Mar. 16, 2011.

(30) Foreign Application Priority Data

Apr. 30, 2010 (JP) .................................. 2010-105754

(51) Int. Cl.
*H01J 40/14* (2006.01)
(52) U.S. Cl.
USPC ...................................... 250/221; 250/227.14
(58) Field of Classification Search
USPC ......... 250/221, 227.14, 227.16–227.2, 201.3, 250/208.1, 239; 356/614, 241.1–241.6; 385/8, 55; 600/437–439, 424–429; 601/2; 606/1, 130
See application file for complete search history.

(56) References Cited

U.S. PATENT DOCUMENTS

| 4,902,129 A * | 2/1990 | Siegmund et al. ......... 356/241.4 |
| 5,573,236 A | 11/1996 | Petocchi et al. |
| 2003/0155489 A1 | 8/2003 | Yasuda et al. |

FOREIGN PATENT DOCUMENTS

| JP | 55-40312 | | 9/1978 |
| JP | 60-217326 | A | 10/1985 |
| JP | 61-102914 | | 7/1986 |
| JP | 63-294825 | A | 12/1988 |
| JP | 2-287117 | A | 11/1990 |
| JP | 8-59022 | A | 3/1996 |
| JP | 2001-327504 | A | 11/2001 |
| JP | 2003-194586 | A | 7/2003 |

OTHER PUBLICATIONS

International Preliminary Report on Patentability together with the Written Opinion dated Dec. 20, 2012 received in related International Application No. PCT/JP2011/056259.
International Search Report dated Jun. 7, 2011 issued in PCT/JP2011/056259.

* cited by examiner

*Primary Examiner* — Que T Le
(74) *Attorney, Agent, or Firm* — Scully, Scott, Murphy & Presser, P.C.

(57) ABSTRACT

An optical potentiometer includes a linear power transmission member, a retaining member configured to retain the power transmission member, and an optical element. An optical property of the optical element continuously varies along a moving direction of the power transmission member. The potentiometer further includes a light source, a light receiving section, a linear light transmitting member and a calculating section. The linear light transmitting member guides the light from the light source and outputs the light to the optical element, and guides light input from the optical element to the light receiving section. The calculating section calculates displacement of the power transmission member based on the electric signal output by the light receiving section.

18 Claims, 17 Drawing Sheets

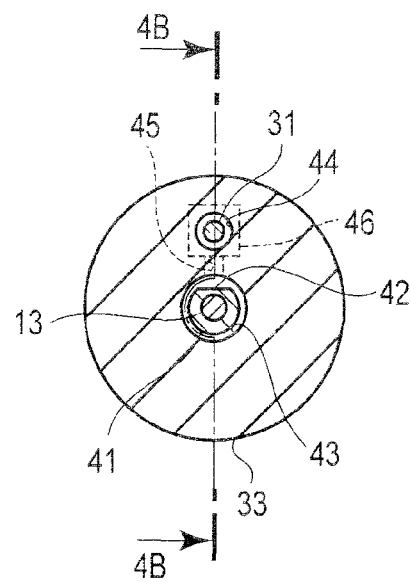
F I G. 4C
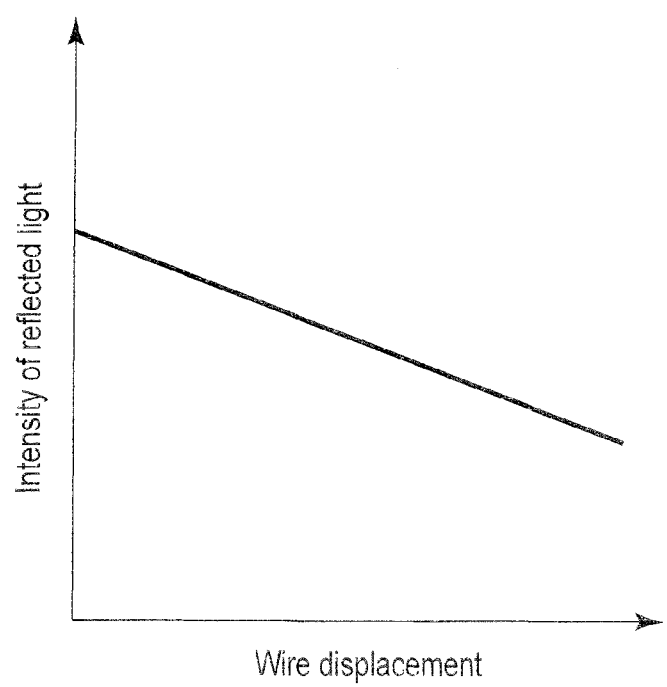
F I G. 5

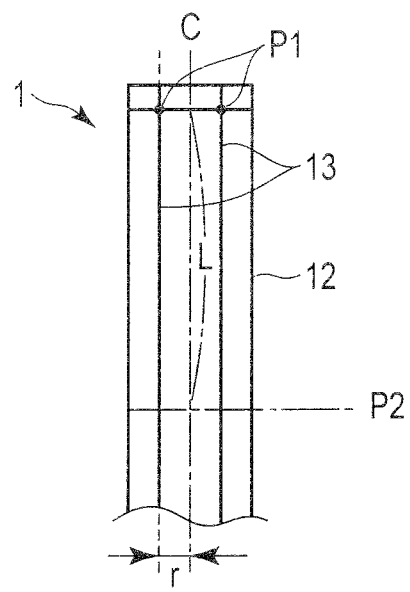
F I G. 6A
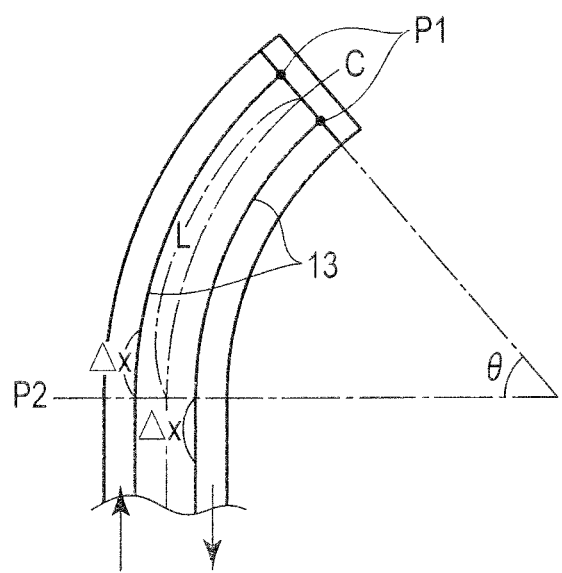
F I G. 6B

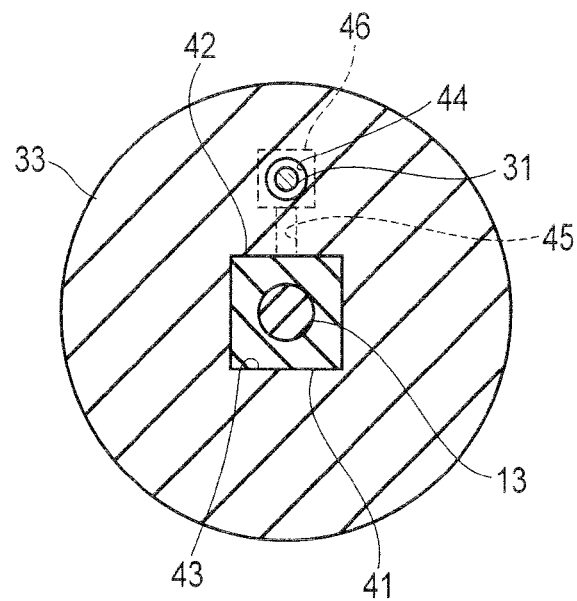
F I G. 8C
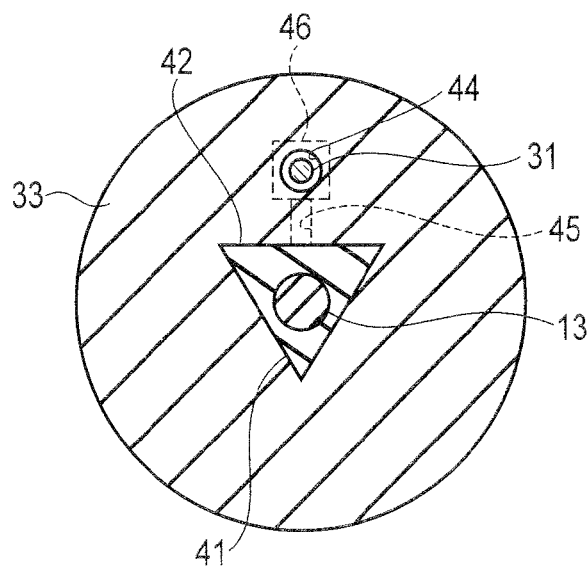
F I G. 8D

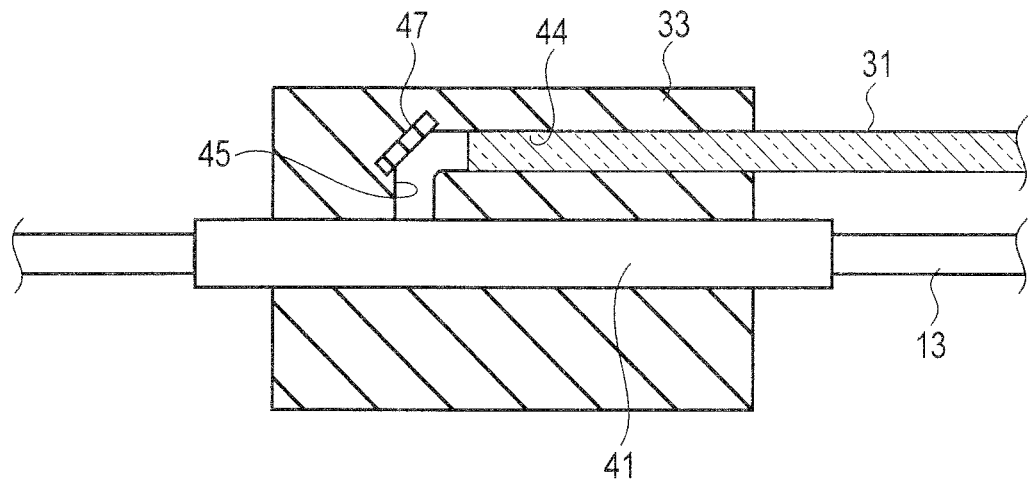
F I G. 9A
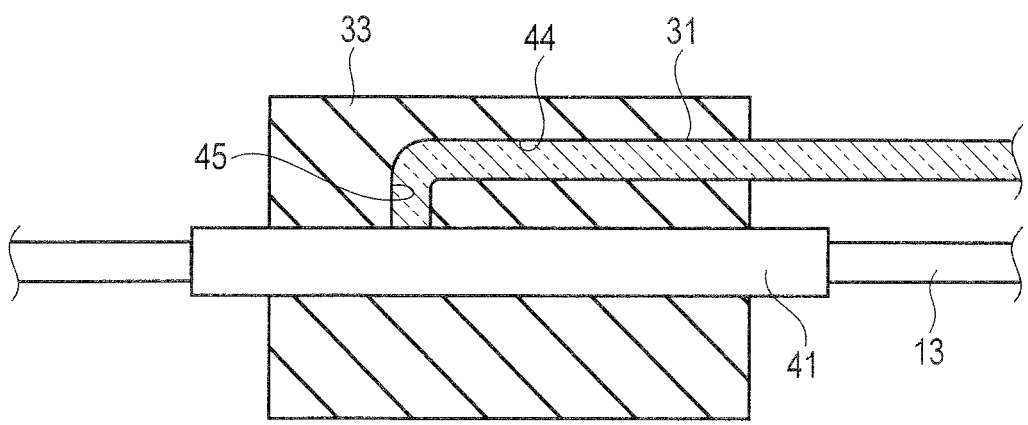
F I G. 9B

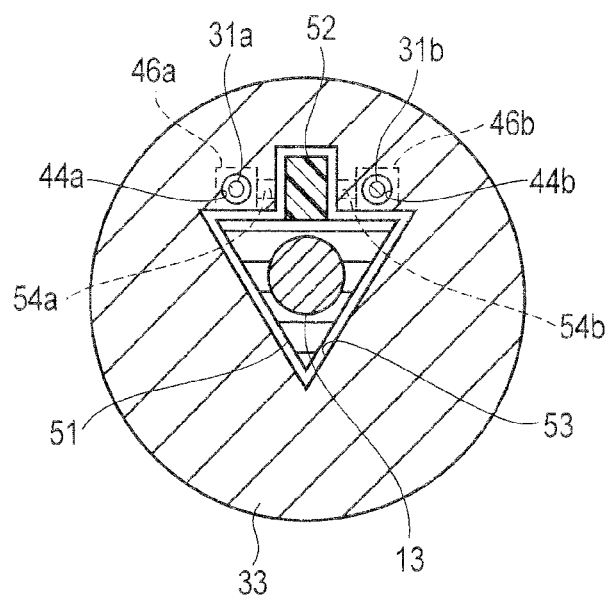
F I G. 15A
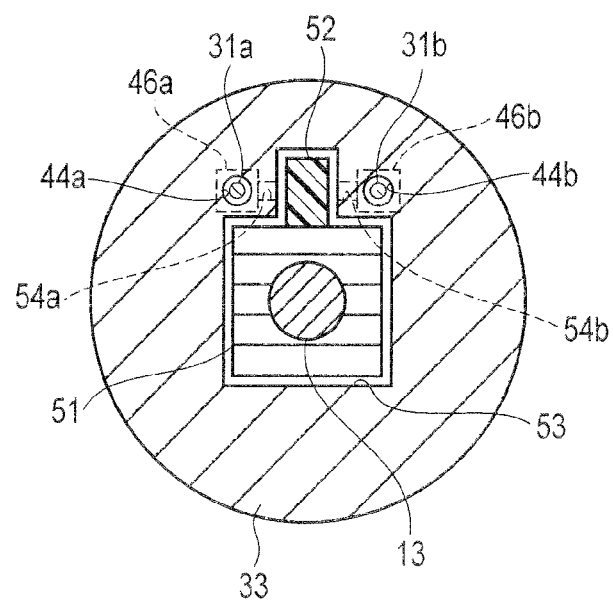
F I G. 15B

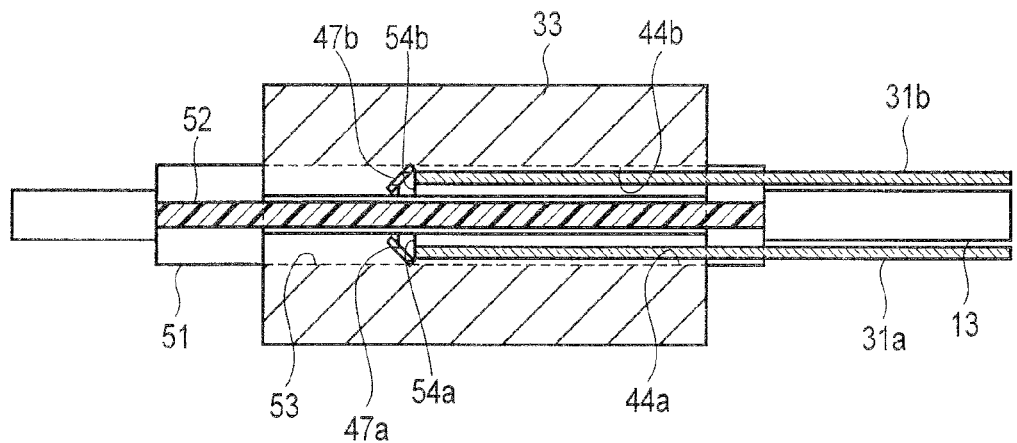
F I G. 16A
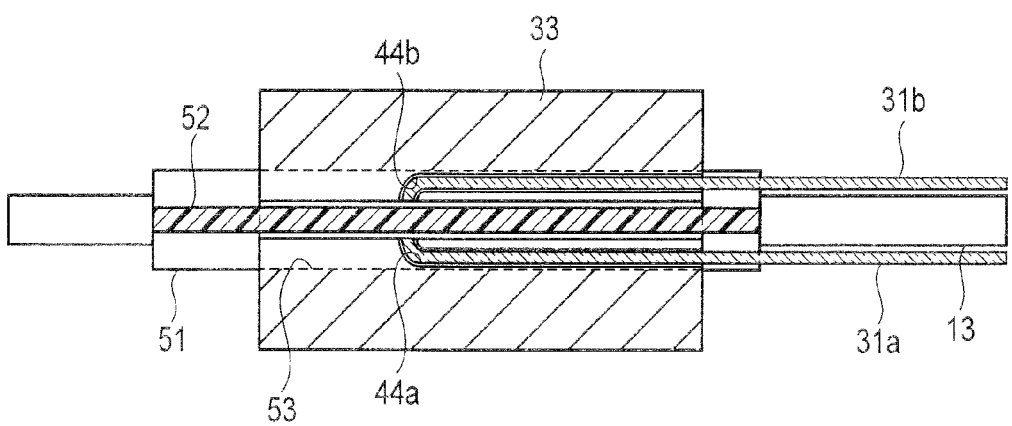
F I G. 16B

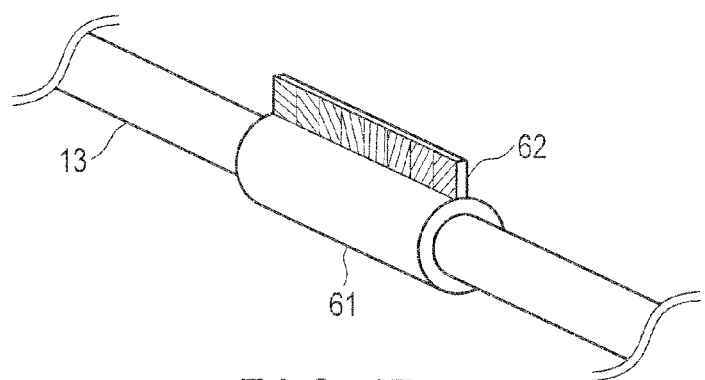
F I G. 17
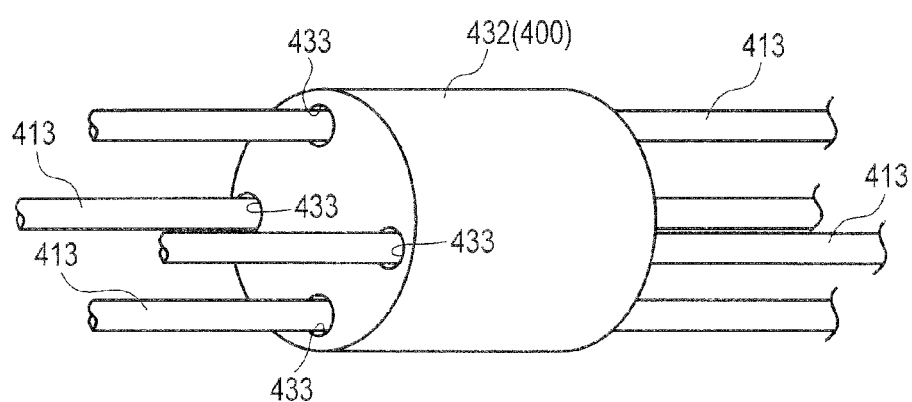
F I G. 18
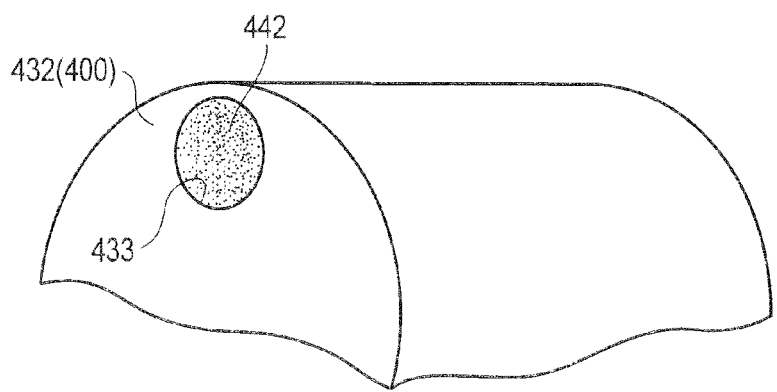
F I G. 19

OPTICAL POTENTIOMETER HAVING AN OPTICAL ELEMENT WITH OPTICAL PROPERTY CONTINUOUSLY VARYING ALONG A MOVING DIRECTION AND OPERATING DEVICE

CROSS REFERENCE TO RELATED APPLICATIONS

This application is a Continuation Application of PCT Application No. PCT/JP2011/056259, filed Mar. 16, 2011 and based upon and claiming the benefit of priority from prior Japanese Patent Application No, 2010-105754, filed Apr. 30, 2010, the entire contents of all of which are incorporated herein by reference.

BACKGROUND OF THE INVENTION

1. Field of the Invention

The present invention relates to an optical potentiometer and an operating device including the same.

2. Description of the Related Art

Generally, an operating device such as an endoscope, a medical manipulator, and a treatment device is provided with an inserting section to be inserted in a patient's body, and to which a bendable moving section is provided. In many of such a moving section, a mechanism that is driven by traction by a linear power transmission member such as a wire is employed. In order to accurately operate the operating device, a unit to detect a bending angle of the moving section needs to be provided. However, since a diameter of the operating device is small, it is difficult to install a conventional potentiometer or encoder. Further, in a case where a freedom of the operating device is high, the number of units to detect those bending angles becomes large accompanying an increase in the number of joints, and electrical wirings to measuring sections of the detecting unit are increased. It is difficult to provide a large number of wirings between machineries and mechanisms within the thin operating device.

An optical potentiometer that does not require an electrical wiring to a measuring section is disclosed for example in Jpn. UM Appln. KOKAI Publication No. 55-40312. The optical potentiometer disclosed in the Jpn. UM Appln. KOKAI Publication No. 55-40312 includes, on a surface of a code disc that is movably supported, a read track whose transmittance varies along a moving direction of the code disc, and a light emitting head and a light receiving head that are arranged opposing one another with the read track intervened in between. This optical potentiometer measures a movement of the code disc by utilizing a change caused by the movement of the code disc in an amount of light that is radiated from the light emitting head and received by the light receiving head by transmitting the read track.

BRIEF SUMMARY OF THE INVENTION

According to an aspect of the present invention, an optical potentiometer comprises a linear power transmission member configured to move in a longitudinal direction; a retaining member configured to retain the linear power transmission member so as to be movable in the longitudinal direction; an optical element, an optical property of the optical element continuously varying along a moving direction of the linear power transmission member; a light source configured to emit light; a light receiving section configured to convert an optical property of input light into an electric signal; a linear light transmitting member configured to guide the light emitted from the light source and output the light to the optical element, and guide light input from the optical element to the light receiving section, an output position of the light emitted from the light source and an input position of the light input from the optical element being retained at certain distances with respect to the optical element; and a calculating section configured to calculate an amount of displacement between the linear power transmission member and the retaining member in the moving direction of the linear power transmission member based on the electric signal output by the light receiving section.

According to an aspect of the present invention, an operating device comprises a tubular member having a long length and a small diameter; a linear power transmission member configured to be inserted through the tubular member; a moving section configured to be arranged at one end of the tubular member, one end of the linear power transmission member being fixed to the moving section, and the moving section bendably moving by a movement of the linear power transmission member in a longitudinal direction; a driving section, the other end of the linear power transmission member being fixed to the driving section, and the driving section moving the linear power transmission member in the longitudinal direction; the above mentioned optical potentiometer configured to measure an amount of displacement of the linear power transmission member; and a computing section configured to calculate a bending angle of the moving section based on the amount of displacement of the linear power transmission member measured by the optical potentiometer.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 4C is a cross sectional diagram showing an example of the configuration of the potentiometer section in the optical potentiometer of the first embodiment.

FIG. 5 is a diagram showing an example of a relationship between a wire displacement and an intensity of reflected light in the optical potentiometer of the first embodiment.

FIG. 6A is a diagram explaining a relationship between the wire displacement and a bending angle of a moving section of a medical manipulator, and is a diagram showing a straightened state.

FIG. 6B is a diagram explaining the relationship between the wire displacement and the bending angle of the moving section of the medical manipulator, and is a diagram showing a bent state.

FIG. 8C is a cross sectional diagram showing an overview of an example of the configuration of the potentiometer section in the optical potentiometer of the second modification of the first embodiment.

FIG. 8D is a cross sectional diagram showing an overview of another example of the configuration of the potentiometer section in the optical potentiometer of the second modification of the first embodiment.

FIG. 9A is a cross sectional diagram showing an overview of an example of a configuration of a potentiometer section in an optical potentiometer of a third modification of the first embodiment.

FIG. 9B is a cross sectional diagram showing an overview of another example of the configuration of the potentiometer section in the optical potentiometer the third modification of the first embodiment.

FIG. 15A is a cross sectional diagram showing an example of a configuration of a potentiometer section in an optical potentiometer of a first modification of the second embodiment.

FIG. 15B is a cross sectional diagram showing another example of the configuration of the potentiometer section in the optical potentiometer of the first modification of the second embodiment.

FIG. 16A is a diagram showing an example of a configuration of a potentiometer section in an optical potentiometer of a second modification of the second embodiment.

FIG. 16B is a diagram showing another example of the configuration of the potentiometer section in the optical potentiometer of the second modification of the second embodiment.

FIG. 17 is a diagram showing an example of a configuration of a polarizing plate supporting section in an optical potentiometer of a third embodiment of the present invention.

FIG. 18 is a perspective diagram showing an overview around a potentiometer linking section in an optical potentiometer of a fourth embodiment of the present invention.

FIG. 19 is a perspective diagram showing an example of a guiding hole of the potentiometer linking section in the optical potentiometer of the fourth embodiment.

DETAILED DESCRIPTION OF THE INVENTION

First Embodiment

The first embodiment of the present invention will be described with reference to the drawings. In the description of the present embodiment, a medical manipulator will, be given as an example of an operating device. Needless to say, the configuration of the present embodiment can similarly be adapted to other operating devices such as an endoscope and a treatment device.

Figure 1:
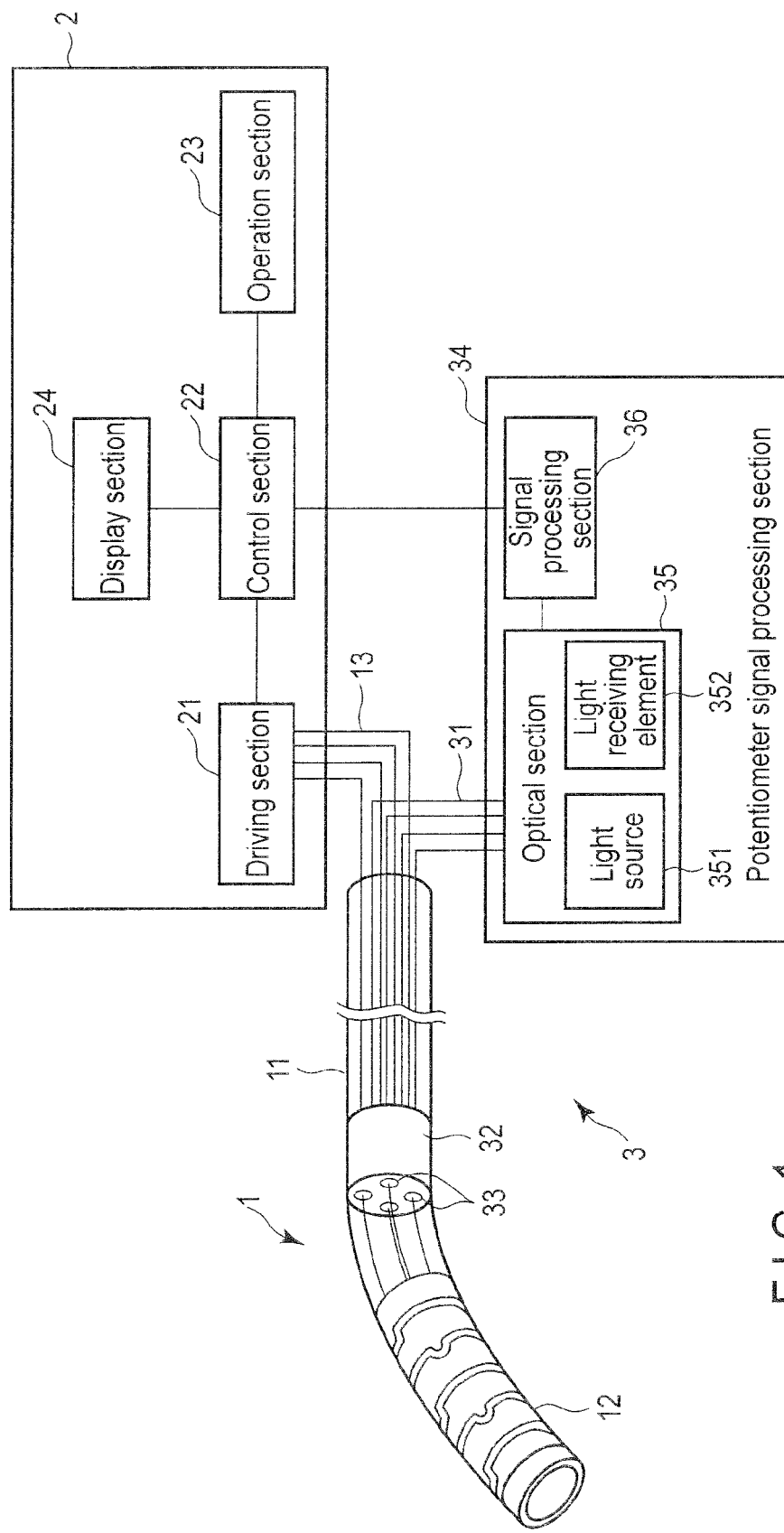
FIG. 1 is an overview diagram of a medical manipulator as a first embodiment of an operating device of the present invention.

As shown in FIG. 1, the medical manipulator as the operating device of the first embodiment of the present invention includes an inserting section 1 to be inserted in a patient's body, a control device 2 that causes the inserting section 1 to be driven, and an optical potentiometer 3 of the first embodiment of the present invention. The inserting section 1 includes a tubular section 11, a moving section 12, and wires 13. The control device 2 includes a driving section 21, a control section 22, an operation section 23, and a display section 24. The optical potentiometer 3 includes optical fibers 31, a potentiometer linking section 32, potentiometer sections 33, and a potentiometer signal processing section 34. The potentiometer signal processing section 34 includes an optical section 35 and a signal processing section 36.

The tubular section 11 for example has a thin and long shape with an outer diameter of 10 mm and a length of 1 to 2 m, and at one end thereof, has the flexibly bendable moving section 12 for example with a length of about 5 to 6 cm. This moving section 12 includes a mechanism that is driven by displacements of the wires 13. That is, the inserting section 1 has holes therewithin that are parallel to their center axis line in a longitudinal direction. The wires 13 pass through the holes in the longitudinal direction of the inserting section 1. Positions of the holes and the wires 13 passing through the holes in a plane that is perpendicular to the center axis of the inserting section 1 in the longitudinal direction (hereinbelow referred to as "circumferential plane") are for example arranged such that two holes are at symmetric positions with respect to a center of the circumferential plane of the inserting section 1, and other two holes are at symmetric positions rotated by 90 degrees from the aforesaid two holes with the center of the circumferential plane of the inserting section 1 as an axis of symmetry. One ends of the four strings of wires 13 respectively passing through the four holes of the inserting section 1 are fixed in the vicinity of an end (distal end side) of the moving section 12 that is not connected to the tubular section 11, and the other ends are connected to the driving section 21 provided on the other end side (proximal end side) of the end of the tubular section 11 to which the moving section 12 is connected. The driving section 21 is for example a combination of a rotary motor and a pulley, or a linear motor. The four strings of wires 13 are respectively connected to the motor and/or the pulley. Alternatively, two strings of wires 13 that are symmetric with respect to the center of the circumferential plane of the inserting section 1 may respectively be formed integrally so as to configure two pairs of wires 13, and the two pairs of wires 13 may each be configured to be wound around different pulleys. This driving section may for example be configured integrally with the inserting section 1, and be connected to the control section such as a computer via connectors that are not shown.

The control section 22 causes the display section 24 configured for example of a display to display an image based on a signal of the image taken by a camera that is not shown by photographing the moving section of the inserting section 1 and a treating portion within the same field of vision. An operator operates the operation section 23 that is for example a joystick or a handle in order to cause the moving section 12 to operate as intended while looking at the image taken by the camera and displayed on the display section 24. The operation section 23 outputs the signal input by the operator to the control section 22. The control section 22 generates a signal for causing the motor of the driving section 21 to drive as required for the movement of the moving section 12 by a predetermined calculating method based on the signal input from the operation section 23, and outputs the signal to the driving section 21. The driving section 21 drives the motor based on the signal input from the control section 22. As a result, the wires 13 are fed out or pulled, and are moved in the longitudinal direction of the inserting section 1.

The moving section 12 bends by the displacements of the wires 13. For example, in a case where one string of wire is pulled while the wire at the symmetric position in the moving section 12 with respect to the center of the circumferential plane is fed out, the moving section 12 bends in a direction where the pulled wire is positioned with respect to the center axis. The moving section 12 can bend flexibly in any direction due to having the two pairs of two strings of wires, the wires being symmetric with respect to the center of the circumferential plane, at the rotational symmetric positions with respect to the center.

For example, the tubular section 11 functions as a long and thin tubular member. For example, the wires 13 function as a linear power transmission member. For example, the moving section 12 functions as a moving section to which one end of the linear power transmission member is fixed, and that bendably moves by a movement of the linear power transmission member in the longitudinal direction. For example, the driving section 21 functions as a driving section to which the other end of the linear power transmission member is fixed, and that moves the linear power transmission member in the longitudinal direction.

As shown in FIG. 1, the cylindrical-shaped potentiometer linking section 32 that is a measuring section in the optical potentiometer of the present embodiment is provided in the vicinity of the moving section 12 in the tubular section 11 of the inserting section 1. In the present embodiment, the potentiometer linking section 32 is provided in the tubular section 11, however, it may be provided as a part of the moving section 12.

Figure 2:
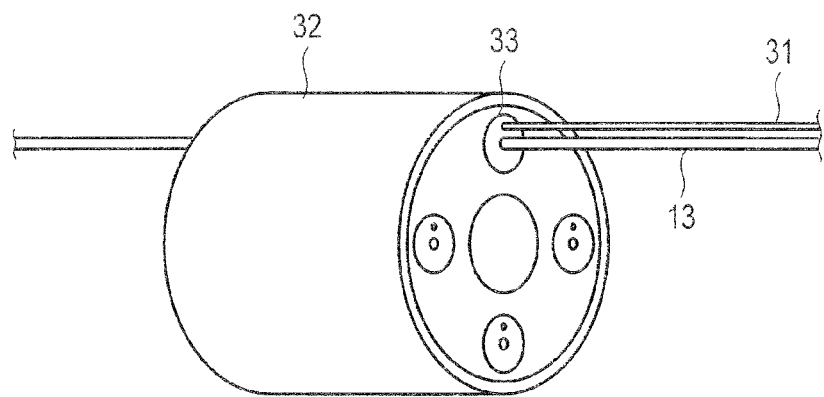
FIG. 2 is a diagram showing an example of a configuration of a potentiometer linking section in the optical potentiometer of the first embodiment of the present invention.

As shown in FIG. 2, the potentiometer linking section 32 includes cylindrical-shaped potentiometer sections 33 that are arranged parallel to a center axis in the longitudinal direction. The number of potentiometer sections 33 is identical to the number of strings of wires 13, which is four in the present embodiment. Positions of the potentiometer sections 33 in the circumferential plane depend on the penetrating positions of the wires 13 in the inserting section 1.

Figure 3A:
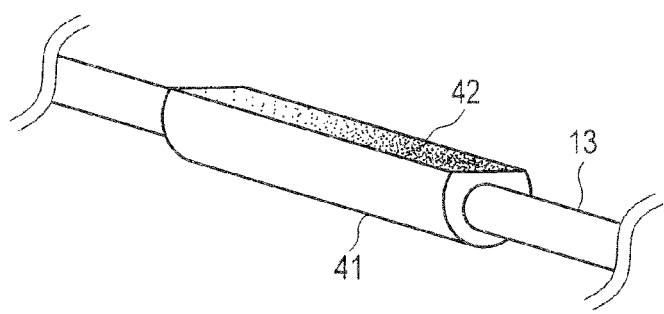
FIG. 3A is a perspective diagram showing an example of a configuration of a reflecting section in the optical potentiometer of the first embodiment.
Figure 3B:
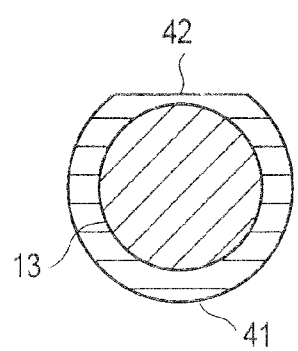
FIG. 3B is a cross sectional diagram showing an example of the configuration of the reflecting section in the optical potentiometer of the first embodiment.
Figure 3C:
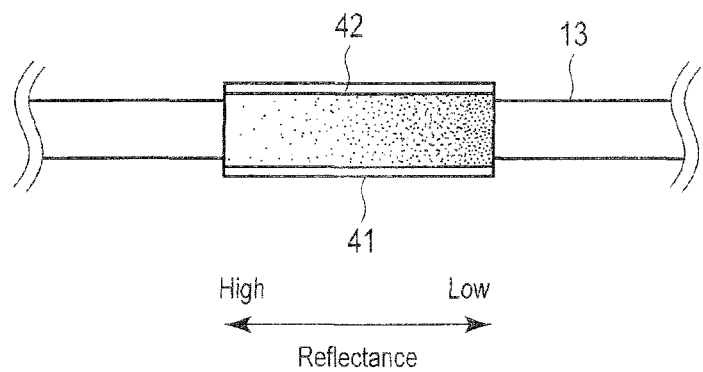
FIG. 3C is a planar diagram showing an example of the configuration of the reflecting section in the optical potentiometer of the first embodiment.

The wires 13 penetrate the potentiometer sections 33. Corresponding to each of the penetrating sections thereof, as shown in FIG. 3A, a reflecting section 41 is provided. FIG. 3A is a perspective diagram of the reflecting section 41. A cross sectional diagram of the reflecting section 41 that is sectioned at the circumferential plane is shown in FIG. 3B. A planar diagram that sees the reflecting section 41 from a direction that opposes a reflecting surface 42 is shown in FIG. 3C. The reflecting section 41 has a shape in which a thin and long cylindrical shape is cut at a plane parallel to a center axis thereof so as to provide a flat surface in the longitudinal direction. The flat surface configures the reflecting surface 42. The reflecting surface 42 has a different optical reflectance according to its position within the surface in the longitudinal direction. In the present embodiment, the optical reflectance of the reflecting surface 42 varies continuously from one end toward the other end in the longitudinal direction of the reflecting surface 42. This reflecting surface 42 is formed for example by forming a member with a constant reflectance on the reflecting section 41 by coating, and thereafter mounting thereon an ND filter whose transmittance continuously varies. Note that, the difference in the reflectance is not limited to an analog continuous variation, but may be a digital continuous variation. That is, the reflectance may vary discretely so long as a required resolution is satisfied. The reflecting section 41 is fixed to the wire with the wire 13 being passed therethrough. Further, the reflecting section 41 (and the reflecting surface 42) may be configured of a member having flexibility and that can bend in accordance with the bending of the wire 13.

For example, the reflecting section 41 functions as a columnar shaped light reflecting body supporting member that has its axis line parallel to the linear power transmission member that moves in the longitudinal direction and has a flat surface parallel to the axis line, or as an optical element supporting member provided so as to be capable of integrally moving with the linear power transmission member. For example, the reflecting surface 42 functions as an optical element having an optical property that continuously varies along the moving direction of the linear power transmission member, or as a light reflecting body having a reflectance that continuously varies along the moving direction.

Figure 4A:
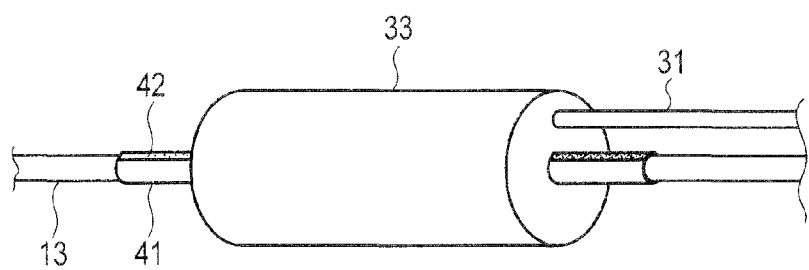
FIG. 4A is a perspective diagram showing an example of a configuration of a potentiometer section in the optical potentiometer of the first embodiment.
Figure 4B:
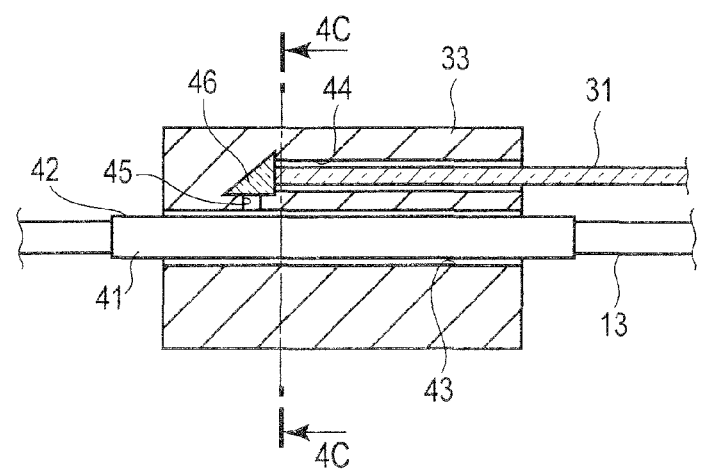
FIG. 4B is a cross sectional diagram showing an example of the configuration of the potentiometer section in the optical potentiometer of the first embodiment.

As shown in FIG. 4A, one end of the optical fiber 31 is introduced into each potentiometer section 33. FIG. 4A shows a perspective diagram of the potentiometer section. A diagram of a cross section along a 4B-4B line shown in FIG. 40 in the longitudinal direction of the potentiometer section 33 is shown in FIG. 4B. A cross section seen along arrows along a 4C-4C line in FIG. 4B is shown in FIG. 4C. The reflecting section 41 fixed to the wire 13 is inserted through a reflecting section hole 43 (supporting member hole) that penetrates the potentiometer section 33 in the longitudinal direction parallel to the center axis thereof, and a fitting structure is formed by the reflecting section hole 43 and the reflecting section 41. The reflecting section 41 can freely slide along the reflecting section hole 43. Further, an optical fiber hole 44 is provided parallel to the reflecting section hole 43 in the potentiometer section 33, and the optical fiber 31 is inserted to the optical fiber hole 44 and fixed therein. An end portion of the optical fiber 31 is present inside the potentiometer section 33. A prism 46 is arranged at a position of the end portion of the optical fiber 31. An optical path hole 45 that is a hole perpendicular to the reflecting section hole 43 is further included inside the potentiometer section 33 between the reflecting section hole 43 and this prism 46. According to this structure, the end portion of the optical fiber 31 and one end of the optical path hole 45 are optically connected by the prism 46.

The optical fiber 31 passes through the tubular section 11, and an end (proximal end side) thereof that is different from the end (distal end side) connected to the potentiometer section 33 is connected to the potentiometer signal processing section 34 that is arranged outside of the end (proximal end side) of the tubular section 11 that is opposite from the end (distal end side) where the moving section 12 is provided, via an optical connector and the like that is not shown. As described above, the potentiometer signal processing section 34 includes the optical section 35 and the signal processing section 36. The optical section 35 includes a light source 351, a lens, and a light receiving element 352. Each of the optical fibers 31 is connected to the optical section 35.

The light source 351 in the optical section 35 is configured to radiate light with a constant intensity. Optical members such as the lens and the like in the optical section 35 guides the light radiated by the light source 351 to each optical fiber 31. The optical fiber 31 propagates the light to the potentiometer section 33. The prism 46 at the end portion of the optical fiber 31 shifts a traveling direction of the light guided by the optical fiber 31 by 90 degrees, and irradiates the light to the reflecting surface 42 of the reflecting section 41 through the optical path hole 45. Here, the optical fiber 31 being retained parallel to the moving direction of the reflecting surface 42, that is, parallel to the wire 13, and the prism 46 being used for the optical path conversion for perpendicularly irradiating the light guided by the optical fiber 31 to the reflecting surface 42 are resulting in making the optical potentiometer of the present embodiment compact.

For example, the light source 351 in the optical section 35 functions as a light source that emits light. For example, the optical fibers 31 function as a linear light transmitting member that guides the light emitted from the light source and outputs the light to an optical element. For example, the prisms 46 function as an optical path changing member that shifts an optical path of the linear light transmitting member towards the optical element.

The reflecting surface 42 reflects the input light. At this occasion, when the wire 13 moves in its longitudinal direction so as to move the moving section 12 of the inserting section 1, the reflecting section 41 fixed to the wire 13 also moves in the longitudinal direction along with the movement of the wire 13. As mentioned above, the reflecting surface 42 provided on the reflecting section 41 has the optical reflectance varying continuously in the longitudinal direction. Contrary to the reflecting surface 42 being moved along with the movement of the reflecting section 41, the end portion of the optical fiber 31, the prism 46, and the optical path hole 45 that output the light to the reflecting surface 42 are fixed to the potentiometer section 33. That is, an output position of the light from the light source 351 is retained in the potentiometer section 33 with a certain distance with respect to the reflecting surface 42. Due to this, the reflectance of the reflecting surface 42 at the portion where the light output toward the reflecting surface 42 is reflected varies in accordance with the displacement of the wire 13. Accordingly, the intensity of the light that is input to and reflected at the reflecting surface 42 varies in accordance with the displacement of the wire 13. Note that, as described above, the reflecting section 41 forms the fitting structure with the reflecting section hole 43 of the potentiometer section 33. Due to this, since the reflecting section 41 does not deform within the potentiometer section 33, an optical path length of the light does not change. An example of a relationship between the displacement of the wire 13 and the intensity of the reflected light is shown in FIG. 5.

For example, the potentiometer sections 33 function as a retaining member that movably retains the portion of the linear power transmission member where the optical element is provided. Further, for example, the potentiometer sections 33 function as a retaining member that retains the output position and an input position of the light to the linear light transmitting unit with certain distances with respect to the optical element.

In the present embodiment, since the linear light transmitting member that guides the light output from the optical section 35 to the reflecting surface 42 is made to serve also as the linear light transmitting member that guides the light reflected at the reflecting surface 42 to the optical section 35, the light reflected at the reflecting surface 42 is guided to the optical section 35 by traveling through the same optical path as that upon the output to the reflecting surface 42. That is, the light reflected at the reflecting surface 42 is input to the prism 46 by traveling through the optical path hole 45. The prism 46 shifts the traveling direction of the reflected light by 90 degrees, and guides the reflected light to the optical fiber 31. The optical fiber 31 propagates the reflected light to the optical section 35. For example, the optical fibers 31 function as a linear light transmitting member that guides the light input from the optical element to the light receiving section.

In the above description, although the optical fiber 31, the prism 46, and the optical members within the optical section 35 as the linear light transmitting member are used, a convex lens, a ball lens and the like that convert the output light from the optical fiber 31 to collimated light may further be provided.

The light receiving element 352 in the optical section 35 receives the light reflected by the reflecting surface 42 and propagated through the optical fiber 31, and generates an electric signal in accordance with the light intensity. The optical section 35 outputs the generated electric signal to the signal processing section 36. The signal processing section 36 performs a predetermined processing such as a waveform processing that is a typical signal processing performed in a potentiometer to the electric signal input from the optical section 35. The signal processing section 36 outputs a signal obtained as a result of the signal processing to the control section 22. The control section 22 calculates an amount of displacement of the wire 13 by using a known relationship between signal and displacement based on the signal input from the signal processing section 36.

In the present embodiment, the output position where the light from the light source 351 is output from the optical fiber 31, and the input position where the light reflected at the reflecting surface 42 is input to the optical fiber 31 are fixed to the potentiometer section 33. Accordingly, the amount of displacement of the wire 13 becomes an amount of displacement between the wire 13 and the potentiometer section 33.

For example, the light receiving element 352 in the optical section 35 functions as a light receiving section that converts an optical property of the light propagated from the optical element into an electric signal. For example, the signal processing section 36 functions as a calculating section that calculates an amount of displacement between the linear power transmission member and the retaining member.

The control section 22 calculates a bending angle of the moving section 12 from the amounts of displacement of the wires 13 calculated as above. There are various methods to calculate the bending angle of the moving section 12 from the amounts of displacement of the wires 13. One method is to measure the bending angle of the moving section 12 while actually changing the amounts of displacement of the wires 13 in various manners, and derive relational expressions thereof. Alternatively, a table of the relationship between the amounts of displacement of the wires 13 and the bending angle of the moving section 12 may be created, and the table may be read. In this way, for example, the control section 22 functions as a computing section that calculates the bending angle of the moving section based on the amount of displacement of the linear power transmission member.

Another method to obtain the bending angle of the moving section 12 from the amounts of displacement of the wires 13 will be described with reference to FIGS. 6A and 6B. As shown in FIG. 6A, wire attaching positions P1 where the wires 13 are attached are provided in the vicinity of the distal end of the moving section 12. The moving section 12 has a bending start position P2 that is at the most proximal end side of a portion that bends when the wires 13 are pulled. A length on a center axis line C between the wire attaching positions P1 and the bending start position P2 will be termed L. A length in a radial direction from the center axis line C to the respective wire attaching positions P1 will be termed r. As shown in FIG. 6B, when the driving section 21 pulls only one of the wires 13 by $\Delta x$ and feeds out the other of the wires 13 by $\Delta x$, since L does not change if a curvature from P1 to P2 is the same at both positions, a relationship of a moving amount $\Delta x$ of the wires 13 with respect to an angle $\theta$ between the bending start position P2 and the wire attaching positions P1 becomes $\theta = \Delta x/r$. Here, a pair of wires 13 that is at symmetric positions with respect to the center of the moving section 12 has been described, however, the above expression stands valid even for a case where a plurality of pairs of wires 13 is simultaneously pulled and fed out. Accordingly, when the displacements of the wires 13 are obtained, a bending amount of the moving section 12 can be obtained.

As described above, the optical potentiometer of the present embodiment is configured by using only the optical members such as the optical fibers 31 and the prisms 46 in the inserting section 1, and the number of potentiometer linking section 32 does not increase even if the number of joints of the moving section increases. Due to this, the optical potentiometer of the present embodiment can be made compact, and can even be installed in a thin medical manipulator having a diameter of 10 mm or less. Further, since no electrical component for the potentiometer is used in the inserting section 1, wirings such as a power line and a signal line are unnecessary, by which a space can be saved. The operating device of the present embodiment can more accurately obtain the actual displacement of the moving section 12 by providing the potentiometer linking section 32 of the optical potentiometer in the vicinity of the moving section 12. When the motor of the driving section 21 is driven while performing a feedback control by using a difference of the actual displacement obtained by the present optical potentiometer and a target displacement, a positioning accuracy of the moving section 12 can be improved.

In the present embodiment, since no electrical component is used in the inserting section 1, the potentiometer linking section 32 that is the measuring section of the optical potentiometer provided in the inserting section 1 is not subjected to an influence of an electric noise during use. Further, due to the same reason, the inserting section 1 can easily be sterilized and washed.

By installing a camera at the distal end of the inserting section 1, the operator can operate the operation section while observing an image in a direction toward which the distal end of the inserting section 1 is facing by the display section 24. By so doing, it becomes easy to cause the moving section 12 to move as intended.

Next, modifications of the present embodiment will be described with reference to the drawings. Here, same reference signs will be given to portions that are identical to the present embodiment, and detailed descriptions thereof will be omitted.

Figure 7:
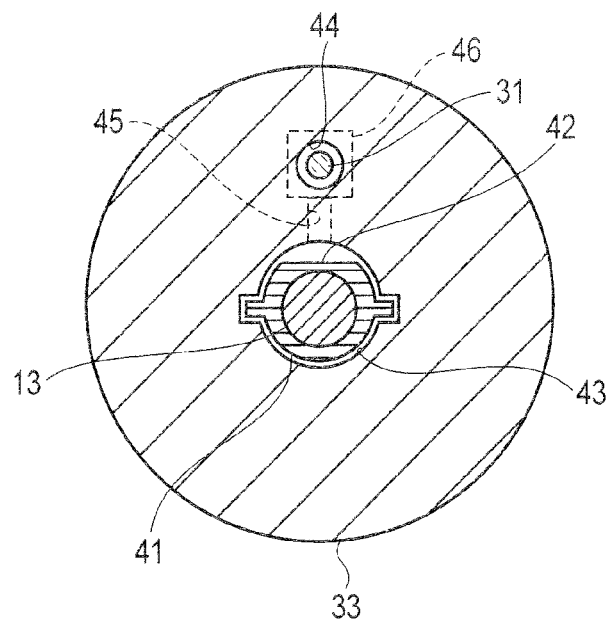
FIG. 7 is a cross sectional diagram showing an example of a configuration of a potentiometer section in an optical potentiometer of a first modification of the first embodiment.

Firstly an optical potentiometer of a first modification of the present embodiment will be described with reference to FIG. 7 that corresponds to FIG. 4C of the present embodiment. In the present modification, in order to prevent a reflecting section 41 from rotating in a circumferential direction with respect to a potentiometer section 33, concave sections and convex sections are provided respectively to the potentiometer section 33 and the reflecting section 41, and the concave sections and convex sections are configured to fit with one another. Shapes shown in FIG. 7 are an example, and any shape may be employed so long as cross sectional shapes of the reflecting section 41 and the potentiometer section 33 are of shapes that fit with one another and do not rotate relative to one another.

Figure 8A:
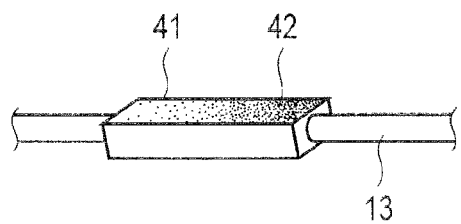
FIG. 8A is a diagram showing an example of a configuration of a potentiometer section in an optical potentiometer of a second modification of the first embodiment.
Figure 8B:
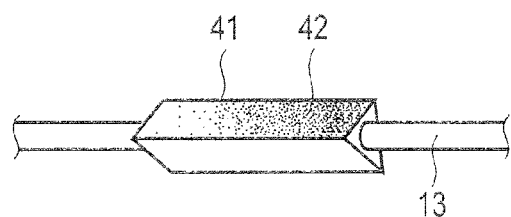
FIG. 8B is a diagram showing another example of the configuration of the potentiometer section in the optical potentiometer of the second modification of the first embodiment.

Next, an optical potentiometer of a second modification of the present embodiment will be described with reference to FIGS. 8A and 8B that correspond to FIG. 3A of the present embodiment. A shape of a reflecting section 41 may be a square column having a hollow through which a wire 13 can be passed as shown in FIG. 8A, or may be a triangular column having a hollow through which the wire 13 can be passed as shown in FIG. 8B. FIGS. 8C and 8D are cross sectional diagrams in the respective cases of FIG. 8A and FIG. 8B corresponding to FIG. 4C of the present embodiment. As shown in these drawings, the reflecting section 41 forms a fitting structure with a potentiometer section 33. According to such a shape, similar to the first modification, a rotation of the reflecting section 41 in a circumferential direction with respect to the potentiometer section 33 can be prevented. As a result, irradiation of light to the reflecting section 41 and receipt of reflected light from the reflecting section 41 can stably be performed.

Note that, in the first embodiment and the first and second modifications thereof, the reflecting section 41 may have a structure of not having the hollow through which the wire 13 is to be passed, and instead fixing wires 13 at both end surfaces of the reflecting section 41 in a longitudinal direction.

Next, an optical potentiometer of a third modification of the present embodiment will be described with reference to FIGS. 9A and 9B that correspond to FIG. 4B of the present embodiment. In the modification shown in FIG. 9A, a prism 46 in a potentiometer section 33 of the present embodiment is replaced by a mirror 47. That is, light output from a light source 351 of an optical section 35 is guided by each optical fiber 31 to the mirror 47. The mirror 47 shifts a traveling direction of the guided light by 90 degrees. The light is irradiated to a reflecting section 41 via an optical path hole 45. Further, in the modification shown in FIG. 9B, the optical fiber 31 passes through an optical fiber hole 44, curves at an end portion of the optical fiber hole 44, and penetrates an optical path hole 45. In either configuration of FIGS. 9A and 9B, the light to be propagated is irradiated perpendicularly to the reflecting surface 42 of the reflecting section 41. The reflected light by the reflecting surface 42 travels through the same optical path as the input light, and is guided by the optical fiber 31 to the optical section 35. In this way, the mirror 47 and the curved section of the optical fiber 31 function as an optical path changing member that directs an optical path of the linear light transmitting member toward the optical element.

Figure 10:
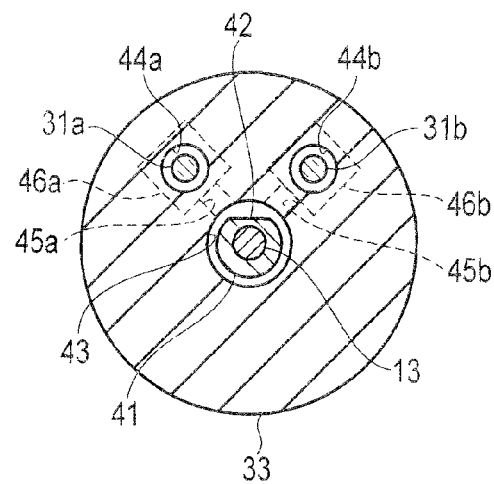
FIG. 10 is a cross sectional diagram showing an example of a configuration of a potentiometer section in an optical potentiometer of a fourth modification of the first embodiment.

Next, an optical potentiometer of a fourth modification of the present embodiment will be described with reference to FIG. 10 that corresponds to FIG. 4C of the present embodiment. In the present modification, an optical path of input light to a reflecting surface 42 and an optical path of reflected light from the reflecting surface 42 are made different. That is, light radiated from a light source 351 in an optical section 35 is guided by an optical fiber 31a. The optical fiber 31a propagates the light to a potentiometer section. A prism 46a at an end portion of the optical fiber 31a shifts a traveling direction of light guided by the optical fiber 31a, and irradiates the light to the reflecting surface 42 of a reflecting section 41 through an optical path hole 45a. The light reflected by the reflecting surface 42 is input to a prism 46b through an optical path hole 45b. The prism 46b shifts a traveling direction of the reflected light, and guides the light to an optical fiber 31b. The optical fiber 31b propagates the reflected light to the optical section 35. As described, for example, the optical fibers 31a function as a first linear light transmitting body that guides light from the light source to the optical element, and for example, the optical fibers 31b function as a second linear light transmitting body that guides light from the optical element to the light receiving section.

The third modification, the fourth modification, and the first or second modifications may respectively be used in combination.

Second Embodiment

The second embodiment of the present invention will be described with reference to the drawings. Here, descriptions will be given focusing on differences from the first embodiment. Same reference signs will be given to portions that are identical to the first embodiment, and descriptions thereof will be omitted.

In the first embodiment, a reflecting surface 42 in which an optical reflectance varies according to positions in a longitudinal direction is provided in each potentiometer section 33. The first embodiment presented an optical potentiometer that irradiates light guided by optical fibers 31 to the reflecting surfaces 42, obtains reflected light, and measures positions of the reflecting surfaces 42 from the reflected light intensity, that is, displacements of wires 13. In the second embodiment, instead of a member having a varying optical reflectance, a member having a varying light transmittance is provided in a potentiometer section 33.

Figure 11:
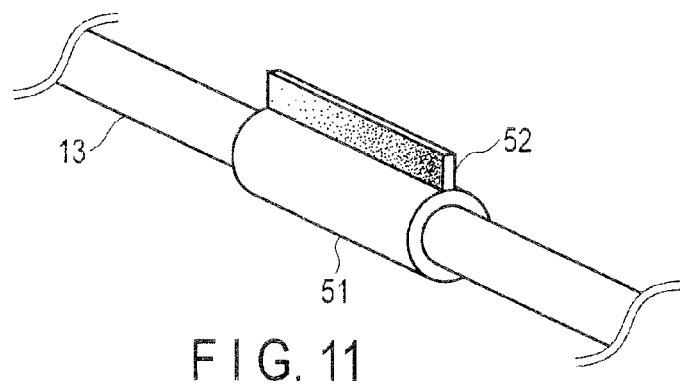
FIG. 11 is a perspective diagram showing an example of a configuration of a transmissive plate supporting section in an optical potentiometer of a second embodiment of the present invention.
Figure 12:
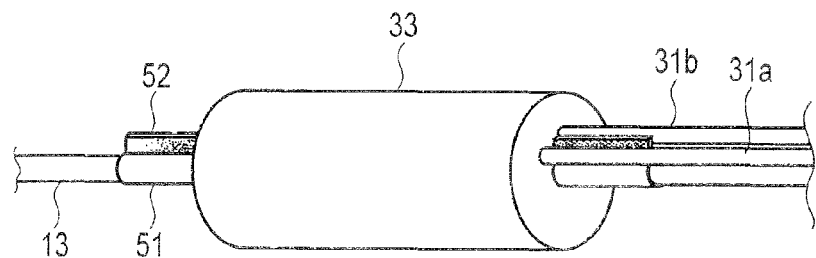
FIG. 12 is a perspective diagram showing an example of a configuration of a potentiometer section in the optical potentiometer in the second embodiment.

That is, as shown in FIG. 11, the optical potentiometer of the present second embodiment includes a transmissive plate supporting section 51 and a transmissive plate 52 instead of a reflecting section 41 in the first embodiment. Each of the transmissive plate supporting sections 51 for example has a thin and long cylindrical shape through which a wire 13 is passed, and supports the transmissive plate 52 at an outside of the cylinder. Each of the transmissive plates 52 for example has a thin and long flat plate shape, and is attached so as to be perpendicular to a circumferential plane of the transmissive plate supporting section 51 and have a longitudinal direction of the transmissive plate 52 be parallel to a center axis of the transmissive plate supporting section 51. The transmissive plate 52 has different light transmittance according to positions along the longitudinal direction. As shown in FIG. 11, in the present embodiment, the light transmittance of the transmissive plate 52 varies continuously from one end to the other end in the longitudinal direction. This difference in the light transmittance may not be an analog continuous variation, but may be a digital continuous variation. The transmissive plate supporting section 51 is fixed to the wire in a manner having the wire 13 passed therethrough. Further, the transmissive plate supporting section 51 and the transmissive plate 52 are formed of materials having flexibility, and bend in accordance with bending of the wire. As described above, for example, the transmissive plate supporting sections 51 function as an optical element supporting member that is provided to be integrally movable with a linear power transmission member. For example, the transmissive plates 52 function as an optical element having an optical property that varies continuously along a moving direction of the linear power transmission member, or a light transmitting body in which transmittance varies continuously along the moving direction.

In the present embodiment, as shown in FIGS. 12, 13A, 13B, and 13C, an optical fiber 31a and an optical fiber 31b are guided through the potentiometer sections 33. The transmissive plate supporting section 51 fixed to the wire 13 penetrates the potentiometer section 33 while being parallel to the center axis in the longitudinal direction, passes through a transmissive plate supporting section hole 53 (supporting member hole) having a shape corresponding to the transmissive plate supporting section 51 and the transmissive plate 52, and a fitting structure is formed by the transmissive plate supporting section 51 and the transmissive plate 52, and the transmissive plate supporting section hole 53. The transmissive plate supporting section 51 and the transmissive plate 52 can freely slide along the transmissive plate supporting section hole 53. The potentiometer section 33 includes an optical fiber hole 44a and an optical fiber hole 44b parallel to the transmissive plate supporting section hole 53. The optical fiber hole 44a and the optical fiber hole 44b are for example at symmetric positions with the transmissive plate 52 through the transmissive plate supporting section hole 53 as a symmetric axis. The optical fiber 31a and the optical fiber 31b are respectively inserted and fixed in the optical fiber hole 44a and the optical fiber hole 44b. The potentiometer section 33 has, within its inside, a prism 46a and a prism 46b at respective positions that are end portions of the optical fiber hole 44a and the optical fiber hole 44b, and that oppose one another with the transmissive plate 52 intervened in between. The potentiometer section 33 includes an optical path hole 54a and an optical path hole 54b at respective positions connecting the prism 46a and the prism 46b. The prism 46a and the prism 46b shift optical paths by 90 degrees so as to connect the optical paths of the optical fiber 31a and the optical fiber 31b with the transmissive plate 52, the optical path hole 54a and the optical path hole 54b intervened in between.

Similar to the first embodiment, each optical fiber 31a propagates the light radiated by a light source 351 in the optical section 35 to the potentiometer section. The prism 46a at the end portion of the optical fiber 31a shifts a traveling direction of the light guided by the optical fiber 31a by 90 degrees, and irradiates the light to the transmissive plate 52 through the optical path hole 54a.

Figure 14:
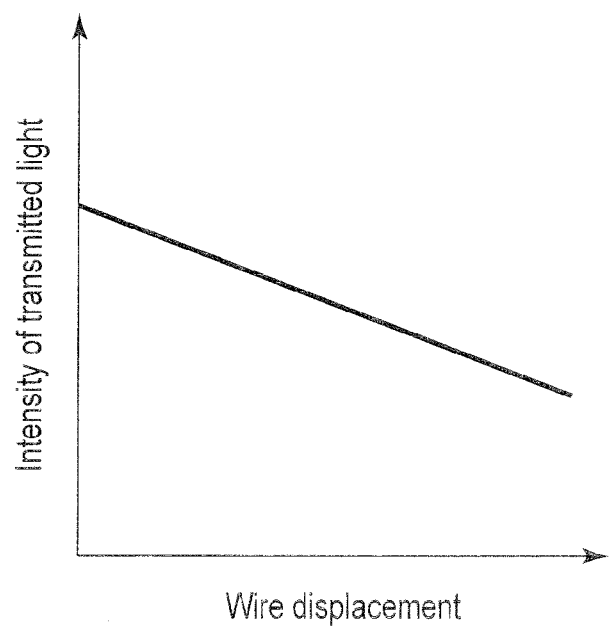
FIG. 14 is a diagram showing an example of a relationship between a wire displacement and an intensity of transmitted light in the optical potentiometer of the second embodiment.

The input light is transmitted through the transmissive plate 52. At this occasion, when the wire 13 moves in its longitudinal direction so as to move the moving section 12 of the inserting section 1, the transmissive plate supporting section 51 fixed to the wire 13 also moves in the longitudinal direction accompanying the movement of the wire 13. Since the light transmittance of the transmissive plate 52 provided on the transmissive plate supporting section 51 varies continuously in the longitudinal direction, an intensity of the transmitted light that is input to and transmitted through the transmissive plate 52 varies in accordance with a displacement of the wire 13. The transmissive plate 52 forms the fitting structure with the transmissive plate supporting section hole 53 of the potentiometer section 33, whereby does not deform within the potentiometer section 33, so the optical path does not change. An example of the relationship between the displacement of the wire 13 and the intensity of the transmitted light is shown in FIG. 14.

The light that is transmitted through the transmissive plate 52 passes through the optical path hole 54b, and is input to the prism 46b. The prism 46b shifts a traveling direction of the transmitted light by 90 degrees, and guides the transmitted light to the optical fiber 31b. The optical fiber 31b propagates the transmitted light to the optical section 35. The transmitted light propagated to the optical section 35 is subjected to a signal processing similar to the first embodiment. As a result, the displacement of the wire 13 is obtained. In this way, for example, the optical fibers 31a function as a first linear light transmitting body that guides light from a light source and outputs the light to a light transmitting body. For example, the optical fibers 31b function as a second linear light transmitting body that inputs the light having transmitted the light transmitting body and guides the light to the light receiving section.

Similar to the first embodiment, in the optical potentiometer of the present embodiment, only optical members such as the optical fibers and the prisms are used in the inserting section 1, and no electrical component is used. Due to this, wirings such as a power line and a signal line are not required. Further, even if a number of joints of the moving section is increased, the number of potentiometer linking section 32 is not increased. Thus, the optical potentiometer of the present embodiment can save space. Further, similar to the first embodiment, in the present embodiment, the actual displacement of the moving section 12 can more accurately be obtained by providing the potentiometer linking section of the optical potentiometer in the vicinity of the moving section 12. As a result, a positioning accuracy of the inserting section 1 can be improved.

Since no electrical component is used in the inserting section 1, the potentiometer linking section that is the measuring section of the optical potentiometer provided in the inserting section 1 is not subjected to an influence of an electric noise during use. Further, the inserting section 1 can easily be sterilized and washed.

Next, modifications of the second embodiment will be described with reference to the drawings. Here, same reference signs will be given to portions that are identical to the present embodiment, and detailed descriptions thereof will be omitted.

Figure 13A:
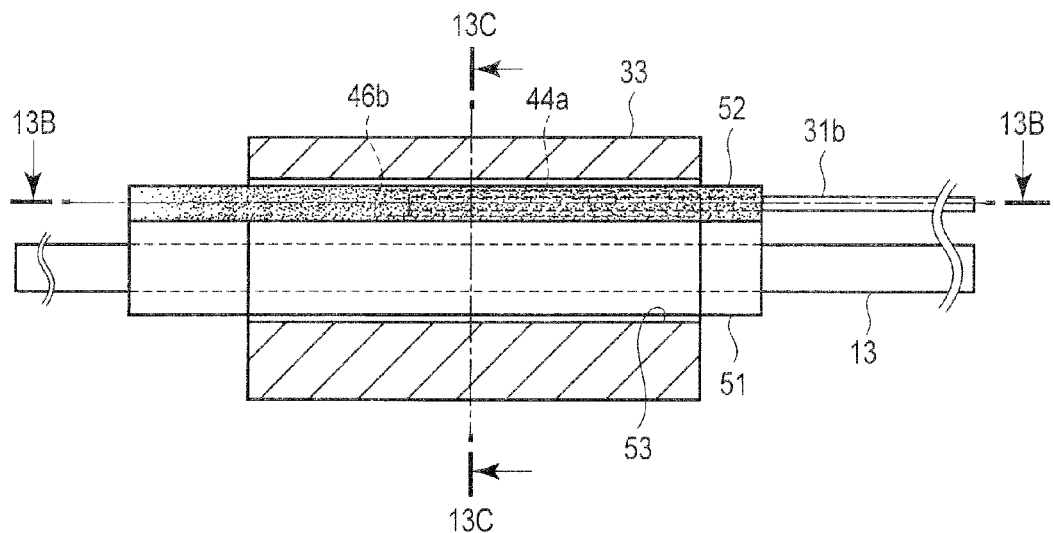
FIG. 13A is a cross sectional diagram showing an example of the configuration of the potentiometer section in the optical potentiometer in the second embodiment.
Figure 13B:
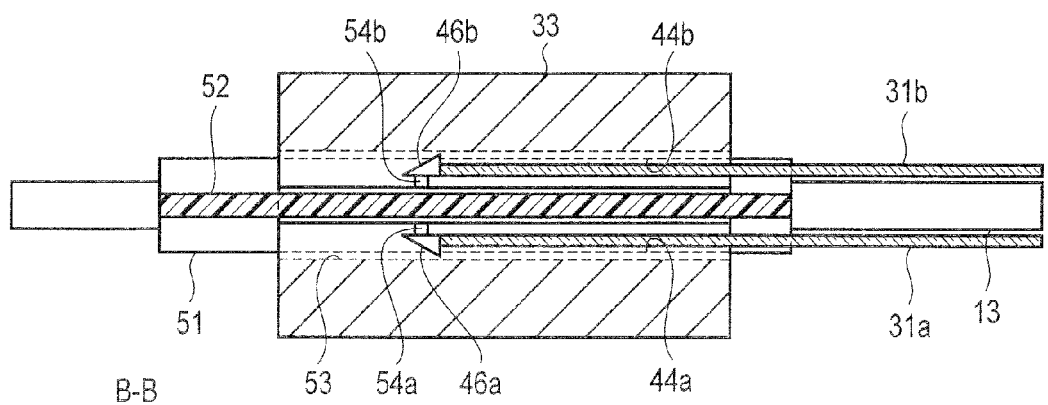
FIG. 13B is a cross sectional diagram showing an example of the configuration of the potentiometer section in the optical potentiometer in the second embodiment.
Figure 13C:
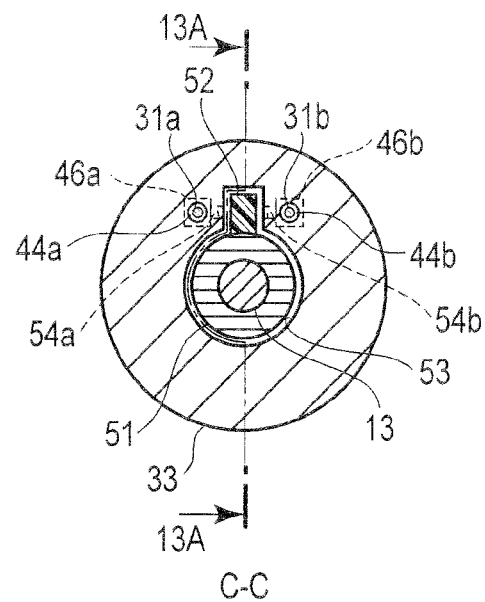
FIG. 13C is a cross sectional diagram showing an example of the configuration of the potentiometer section in the optical potentiometer in the second embodiment.

FIGS. 15A and 15B correspond to FIG. 13C of the present embodiment. As shown in these FIGS. 15A and 15B, an optical potentiometer of a first modification of the present embodiment has a transmissive plate supporting section in a shape of a triangular column or a rectangular column, instead of a round column. Similar to the first embodiment and the modifications thereof, a transmissive plate supporting section 51 may not have a hollow through which a wire 13 passes, and may have a structure of fixing wires 13 on both end surfaces of the transmissive plate supporting section 51 in a longitudinal direction.

Next, an optical potentiometer of a second modification of the present embodiment will be described with reference to FIGS. 16A and 16B corresponding to FIG. 13B of the present embodiment. Similar to the second modification of the first embodiment, as shown in FIG. 16A, in this second embodiment also, prisms 46a and 46b of a potentiometer section 33 may respectively be replaced by mirrors 47a and 47b, or as shown in FIG. 16B, optical fibers 31a and 31b may be curved.

In the case of replacing with the mirrors 47a and 47b, light output from a light source 351 of an optical section 35 is guided by the optical fiber 31a to the mirror 47a. The mirror 47a shifts a traveling direction of the guided light by 90 degrees. The light passes through an optical path hole 54a, is transmitted through a transmissive plate 52, passes through an optical path hole 54b, and reaches the mirror 47b. The mirror 47b shifts a traveling direction of the light by 90 degrees, and guides the light to the optical fiber 31b.

In the case of curving the optical fibers 31a and 31b, the optical fibers 31a and 31b respectively pass through optical fiber holes 44a and 44b, curve at end portions of the optical fiber holes 44a and 44b, and respectively pass through optical path holes 54a and 54b.

In either configuration, light to be propagates is transmitted through a transmissive plate 52 perpendicularly with respect to the transmissive plate 52.

The second modification may be used in combination with the first modification.

Third Embodiment

The third embodiment of the present invention will be described with reference to the drawings. Here, descriptions will be given focusing on differences from the second embodiment. Same reference signs will be given to portions that are identical to the second embodiment, and descriptions thereof will be omitted.

In the second embodiment, transmissive plates 52 having a light transmittance that varies in accordance with positions in a longitudinal direction are provided in potentiometer sections 33. As the second embodiment, an optical potentiometer that irradiates light guided by optical fibers 31a to the transmissive plates 52, obtains transmitted light, and measures positions of the transmissive plates 52, that is, displacements of wires 13 from an intensity of the transmitted light was presented. In the third embodiment, instead of a member having a varying light transmittance, a member having a varying polarization property is provided in each potentiometer section 33.

As shown in FIG. 17, the optical potentiometer of the third embodiment respectively replaces a transmissive plate supporting section 51 and a transmissive plate 52 as described in the second embodiment with reference to FIG. 11 to a polarizing plate supporting section 61 and a polarizing plate 62. Other configurations are the same as the second embodiment. The polarizing plate 62 has a polarization property that varies in accordance with positions in its longitudinal direction. In the present embodiment, as shown in FIG. 17, a polarization angle differs discretely at a required resolution in accordance with the positions in the longitudinal direction of the polarizing plate 62. In this way, for example, the polarizing plate supporting sections 61 function as an optical element supporting member provided capable of integrally moving with a linear power transmission member. For example, the polarizing plates 62 function as an optical element having an optical property that differs continuously along a moving direction of the linear power transmission member.

A potentiometer section 33 of the present embodiment is similar to a potentiometer section 33 in the second embodiment as described with reference to FIGS. 12, 13A, 13B and 13C, and modified points thereof are that the transmissive plate supporting section 51 is replaced with the polarizing plate supporting section 61, and the transmissive plate 52 is replaced with the polarizing plate 62, respectively.

Similar to the second embodiment, each optical fiber 31a propagates the light radiated by a light source 351 in an optical section 16 to a potentiometer section. A prism 46a provided at an end portion of the optical fiber 31a is a total reflection prism. The prism 46a shifts a traveling direction of the light guided by the optical fiber 31a by 90 degrees, and irradiates the light through an optical path hole 54a to the polarizing plate 62. The polarizing plate 62 polarizes the input light upon transmission. At this occasion, when the wire 13 moves in its longitudinal direction so as to move the moving section 12 of the inserting section 1, the polarizing plate supporting section 61 fixed to the wire 13 also moves in the longitudinal direction accompanying the movement of the wire 13. Since the polarizing plate 62 provided on the polarizing plate supporting section 61 has a polarization angle that varies in the longitudinal direction, the angle of polarization of the transmitted light that is input to and is transmitted through the polarizing plate 62 varies in accordance with a displacement of the wire 13. The light that is transmitted through the polarizing plate 62 passes through an optical path hole 54b, and is input to a prism 46b. The prism 46b is a total reflection prism, which shifts a traveling direction of the light by 90 degrees, and guides the light to the optical fiber 31b. Similar to the second embodiment, the optical fiber 31b propagates the transmitted light to the optical section 35. The optical section 35 is provided with instruments such as a rotating polarizing plate to obtain polarizing angle information, thus can detect the change in the polarizing angle of the transmitted light. By detecting the change in the polarizing angle of the transmitted light, relative displacement information of the wire 13 is obtained. In this way, for example, the optical fibers 31a function as a first linear light transmitting body that guides light from a light source and outputs the light to a light transmitting body. For example, the optical fibers 31b function as a second linear light transmitting body that inputs the light that had been transmitted through the light transmitting body and guides the light to a light receiving section.

Similar to the first and second embodiments, in the optical potentiometer of the present embodiment, only optical elements such as the optical fibers and the total reflection prisms are used, and no electrical component is used in the inserting section 1. Accordingly, wirings such as a power line and a signal line are not required. Further, even if a number of joints of the moving section is increased, the number of optical elements is not increased. As a result, the present optical potentiometer can save space by being made compact. Similar to the first embodiment, in the present embodiment, the actual displacement of the moving section 12 can be obtained more accurately by providing a potentiometer linking section of the optical potentiometer in the vicinity of the moving section 12. As a result, a positioning accuracy of the moving section can be improved. Further, since no electrical component is used in the inserting section 1, the potentiometer linking section that is a measuring section of the optical potentiometer provided in the inserting section 1 is not subjected to an electric noise during use. Further, the present inserting section 1 can easily be sterilized and washed.

Different from the first and second embodiments in which an optical reflectance of reflecting sections 41 or a light transmittance of the transmissive plates 52 varying continuously in accordance with positions thereof in an analog manner, the polarizing angle in each polarizing plate 62 of the present embodiment differs discretely in accordance with the positions thereof. However, due to varying discretely at a required resolution, that is, varying in a digital manner, the displacement detection is possible similar to the first and second embodiments. Further, since the polarization property is used in the present embodiment, corrections in accordance with a change in a light intensity such as a change in an intensity of radiated light at a light source or an attenuation of the light intensity at the optical member that may be required in the first and second embodiments is not required in the present embodiment.

Modifications of the present embodiment may be similar to the modifications of the second embodiment. That is, in a first modification, a potentiometer section 33 is not limited to a round column shape, but may have a shape of a triangular column or a rectangular column, similar to the first modification of the second embodiment described with reference to FIGS. 15A and 15B. Further, similar to the first embodiment and the modifications thereof, a polarizing plate supporting section 61 may not have a hollow through which a wire 13 passes, and may have a structure of fixing wires 13 on both end surfaces of the polarizing plate supporting section 61 in a longitudinal direction.

In a second modification, similar to the second modification of the second embodiment described with reference to FIG. 16A, total reflection prisms 46a, 46b of the potentiometer section 33 may be replaced by mirrors 47a, 47b. Similar to the second modification of the second embodiment described with reference to FIG. 16B, optical fibers 31a and 31b may respectively pass through optical fiber holes 44a and 44b, curve at end portions of the optical fiber holes 44a and 44b, and respectively pass through optical path holes 54a and 54b.

The second modification may be used in combination with the first modification.

Fourth Embodiment

The fourth embodiment of the present invention will be described with reference to the drawings. Here, descriptions will be given focusing on differences from the first embodiment. Same reference signs will be given to portions that are identical to the first embodiment, and descriptions thereof will be omitted.

In the first embodiment, reflecting surfaces 42 that function as an optical element or a light reflecting body are provided on wires 13 that function as a linear power transmission member. Optical fibers 31 that function as a linear light transmitting member are retained on potentiometer sections 33 that function as a retaining member that retains an output position and an input position of light of the linear light transmitting member at a certain distance with respect to the optical element. In the fourth embodiment, optical fibers 31 that function as the linear light transmitting member are retained on wires 413 that function as the linear power transmission member, and reflecting surfaces 442 that function as the optical element or the light reflecting body are provided on an optical potentiometer 400 that functions as a retaining member movably retains the wires 413. In the fourth embodiment, the optical potentiometer 400 and the potentiometer linking section 432 are formed integrally. The optical potentiometer 400 and the potentiometer linking section 432 may be separate components, and the optical potentiometer 400 may be assembled to the potentiometer linking section 432.

A schematic view around the potentiometer linking section 432 is shown in FIG. 18. As shown in FIG. 18, the potentiometer linking section 432 includes four guiding holes 433. The guiding holes 433 linearly penetrate the potentiometer linking section 432. Four strings of wires 413 pass through the four guiding holes 433, respectively. The wires 413 are capable of moving in a longitudinal direction with respect to the potentiometer linking section 432. The wires 413 move linearly at least within a range where the reflecting surfaces 442 to be described later are positioned.

Figure 20:
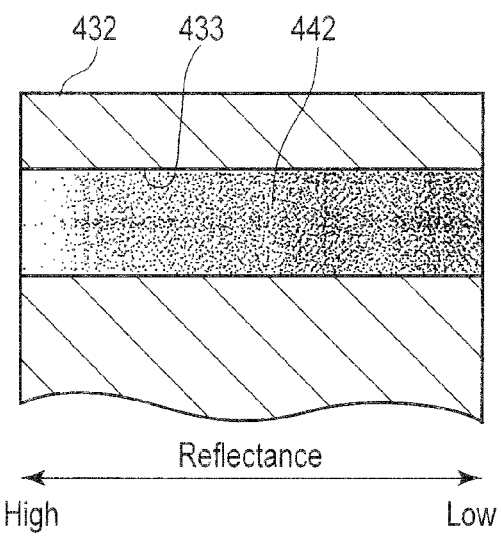
FIG. 20 is a cross sectional diagram showing an example of the potentiometer linking section along the guiding hole in the optical potentiometer of the fourth embodiment.

One guiding hole 433 of the potentiometer linking section 432 is shown in FIG. 19. A cross section of the potentiometer linking section 432 along the guiding hole 433 is shown in FIG. 20. As shown in FIG. 19 and FIG. 20, the reflecting surface 442 is formed at an entire circumference of an inner surface of the guiding hole 433. Similar to the first embodiment, the reflecting surface 442 has an optical reflectance that varies in accordance with positions in a longitudinal direction within its surface. The optical reflectance of the reflecting surface 442 varies continuously from one end in the longitudinal direction of the reflecting surface 442 toward the other end.

Figure 21:
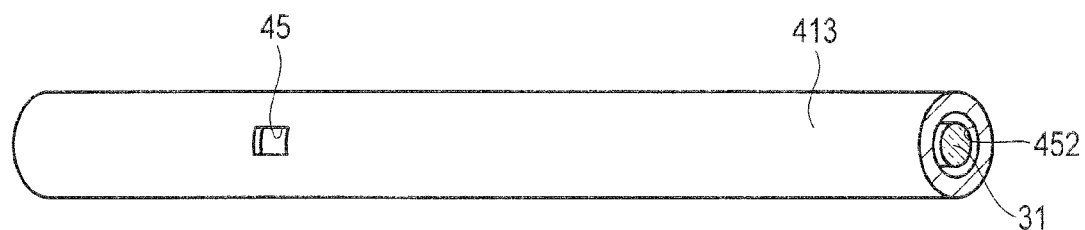
FIG. 21 is a diagram showing an example of a cross section in a radial direction of a wire in the optical potentiometer of the fourth embodiment.
Figure 22:
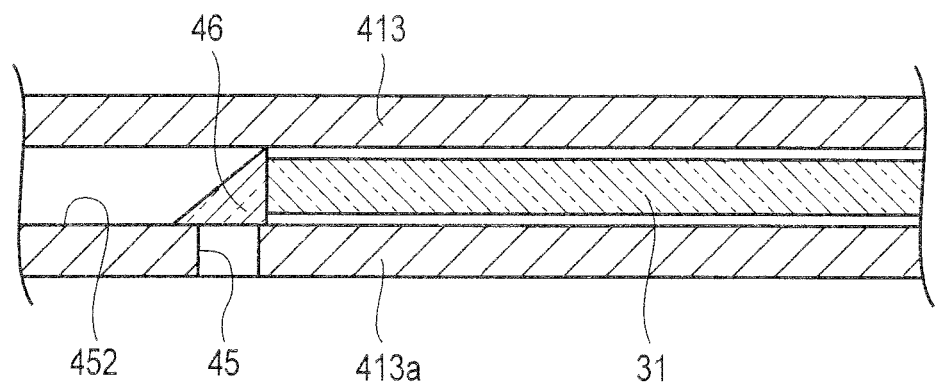
FIG. 22 is a diagram showing an example of a cross section in an axial direction of the wire in the optical potentiometer of the fourth embodiment.

One wire 413 is shown in FIG. 21 and FIG. 22, FIG. 21 is a perspective diagram showing a cross section of the wire 413 in a radial direction. FIG. 22 is a cross sectional diagram of the wire 413 in an axial direction. As shown in FIG. 21 and FIG. 22, the wire 413 is configured of a hollow wire, and includes a hollow section 452 that extends along an entire length of the wire. At least a part of an optical fiber 31 is passed through inside the hollow section 452 of the wire 413. A prism 46 that is an optical path changing member that serves to bend an optical path of light irradiated from the optical fiber 31 is provided at a position on a distal end side of the optical fiber 31 within the hollow section 452 of the wire 413. The prism 46 for example shifts the light irradiated from the optical fiber 31 by 90°. The wire 413 includes an optical path hole 45 that is a light transmissive section that enables the light to propagate between the prism 46 and an external space of the wire 413. Here, an optical path changing member includes an element that bends the optical path by polarization and an element that bends the optical path by reflection, and the prism 46 may be replaced by a mirror and the like.

Figure 23:
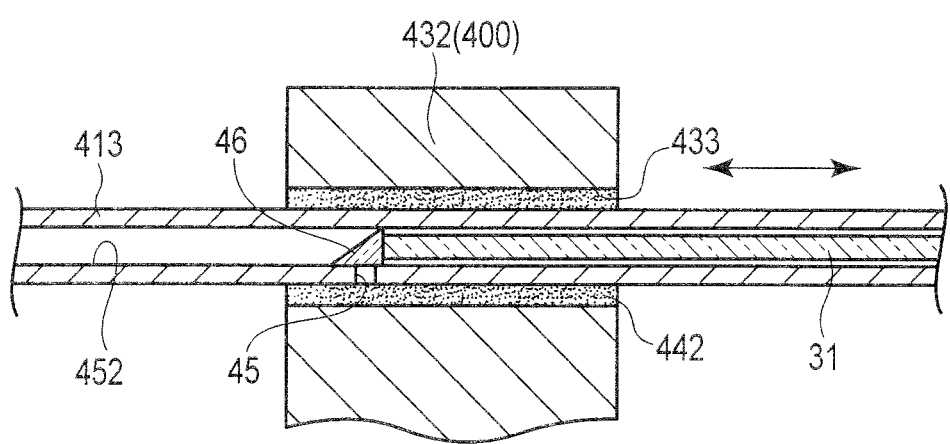
FIG. 23 is a diagram showing an example of cross sections of the potentiometer linking section and the wire in the optical potentiometer of the fourth embodiment.

A cross section of the potentiometer linking section 432 and the wire 413 is shown in FIG. 23. As shown in FIG. 23, the optical path hole 45 formed in the wire 413 opposes the reflecting surface 442. In FIG. 23, for an easier view of the reflecting surface 442, a space is provided between an outer circumferential surface of the wire 413 and the reflecting surface 442, however, the wire 413 and the guiding hole 433 are in fact configured slidable in the longitudinal direction.

When the wire 413 is moved in its longitudinal direction so as to move (bend) a moving section 12 of the inserting section 1 shown in FIG. 1, the optical fiber 31 and the prism 46 move with the wire 413. As a result, as shown in the first embodiment, the optical fiber 31 irradiates light emitted from a light source 351 to the reflecting surface 442, and transmits the light reflected at the reflecting surface 442 to a light receiving section. At this occasion, relative positions of the potentiometer linking section 432 and the wire 413 change.

Figure 24:
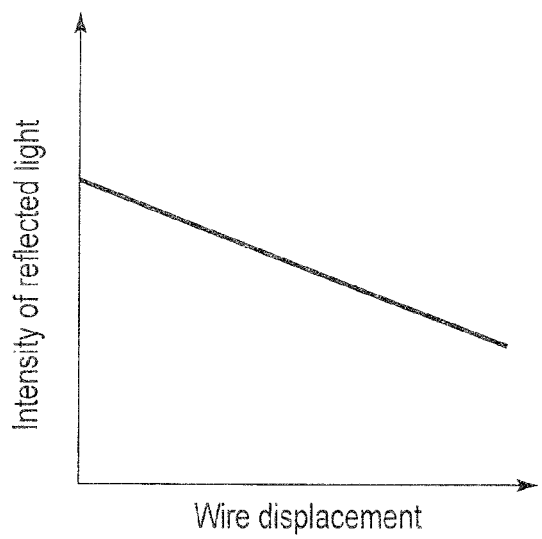
FIG. 24 is a diagram showing an example of a relationship between a wire displacement and an intensity of reflected light in the optical potentiometer of the fourth embodiment.

Accordingly, since the reflecting surface 442 provided in each guiding hole 433 of the potentiometer linking section 432 has its optical reflectance change continuously in the longitudinal direction, an intensity of the light that is input to and reflected at the reflecting surface 442 varies in accordance with a displacement of the wire 413. An example of a relationship between the displacement of the wire 413 and the intensity of the reflected light is shown in FIG. 24.

As described above, the optical fiber 31 (and the prism 46) are retained in the hollow section 452 of each wire 413. An output position and an input position of the light of the linear light transmitting member via a surrounding wall 413a of the wire 413 that is a hollow wire have certain distances with respect to the optical element. The wire 413 is slidably retained on the potentiometer linking section 432 (optical potentiometer 400). In this way, the potentiometer linking section 432 (optical potentiometer 400) functions as the retaining member.

For example, the wires 413 function as the linear power transmission member. For example, the reflecting surfaces 442 function as the optical element having an optical property that varies continuously along a moving direction of the linear power transmission member. For example, the potentiometer linking section 432 (optical potentiometer) to which the reflecting surfaces 442 are provided functions as the retaining member that retains the linear power transmission member so as to be movable in the longitudinal direction.

A method to calculate a bending angle of the moving section 12 from the displacements of the wires 413 is as described in the first embodiment, thus a description therefor is omitted.

In the present fourth embodiment, the optical fibers 31 as the linear light transmitting member pass through the hollow sections 452 of the wires 413. Due to this, there is no need to newly ensure a space for arranging the linear light transmitting member. Thus, according to the present embodiment, the inserting section 1 can easily be made compact and to have a small diameter. Further, since the reflecting surfaces 442 are formed at the inner surfaces of the guiding holes 433 that linearly penetrate the potentiometer linking section 432, linear moving amounts of the wires 413 can be detected. By configuring the wires 413 with the hollow wires, processing thereof is easy, and a cost perspective thereof is also satisfactory. Since a loss is small with the optical fibers 31 when they are bent, so the displacements can surely be detected. Since the optical fibers 31 can easily be made very thin, further downsizing and thinning are enabled.

Figure 25A:
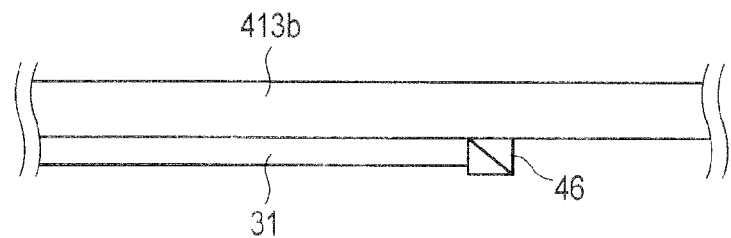
FIG. 25A is a lateral diagram showing an example of a primary part of a modification of a potentiometer linking section and a wire in the optical potentiometer of the fourth embodiment.
Figure 25B:
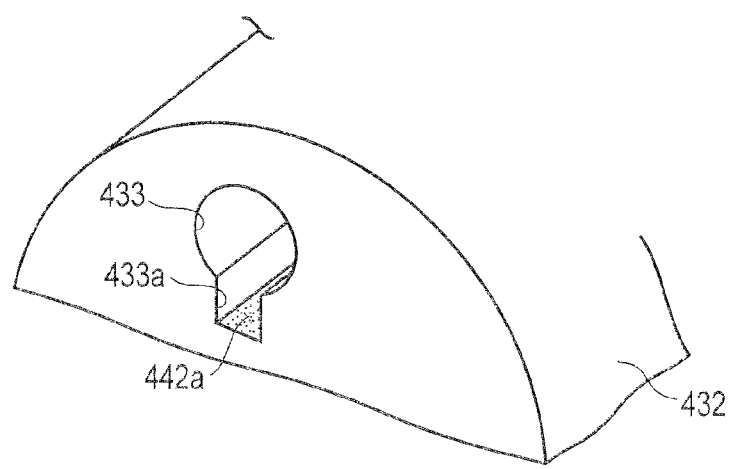
FIG. 25B is a perspective diagram showing an example of the primary part of the modification of the potentiometer linking section and the wire in the optical potentiometer of the fourth embodiment.

Instead of being configured of the hollow wires, the wires 413 may be configured of metal pipes, or coil pipes. The wires 413 may not necessarily have the hollow sections 452 at the entire length thereof, and may have a configuration of partially having the hollow sections 452. Further, the wires 413 may not have the hollow sections 452, and as shown in FIG. 25A, the optical fiber 31 may extend along a wire 413b, and a prism 46 may be provided at one end surface thereof. In this case, a cross sectional shape of a guiding hole 433 of a potentiometer linking section 432 is substantially similar to a cross sectional shape of the optical fiber 31 and the wire 413b as in FIG. 25B. A reflecting surface 442a may be formed at an inner surface of a guiding hole 433a on an optical fiber 31 side.

Further, although the reflecting surface 442 is directly provided on the inner surface of the guiding hole 433, a separate component onto which the reflecting surface 442 is formed or an optical element may be attached to the inner surface. The reflecting surface 442 does not need to be provided at an entire circumference of the guiding hole 433, but may be provided at a part thereof.

The present invention has been described above based on embodiments, however, the present invention is not limited specifically to the above described embodiments, but in actual implementations, may be implemented with modifications to its constituent features within a scope that does not go beyond its essence. For example, the above described embodiments had been given with a medical manipulator as an example, however, similar adaptations to other operating devices such as an endoscope and a treatment device may be made.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An optical potentiometer comprising:
a linear power transmission member configured to move in a longitudinal direction;
a retaining member configured to retain the linear power transmission member so as to be movable in the longitudinal direction;
an optical element, an optical property of the optical element continuously varying along a moving direction of the linear power transmission member;
a light source configured to emit light;
a light receiving section configured to convert an optical property of input light into an electric signal;
a linear light transmitting member configured to guide the light emitted from the light source and output the light to the optical element, and guide light input from the optical element to the light receiving section, an output position of the light emitted from the light source and an input position of the light input from the optical element being retained at certain distances with respect to the optical element; and
a calculating section configured to calculate an amount of displacement between the linear power transmission member and the retaining member in the moving direction of the linear power transmission member based on the electric signal output by the light receiving section.

2. The optical potentiometer according to claim 1, wherein the optical element is provided at a part of the linear power transmission member so as to be integrally movable with the linear power transmission member, and
the linear light transmitting member is retained by the retaining member in which the output position and the input position are provided.

3. The optical potentiometer according to claim 2, wherein the optical element is a light reflecting body, a reflectance of the light reflecting body continuously varying along the moving direction.

4. The optical potentiometer according to claim 3, further comprising:
a columnar-shaped optical element supporting member, an axis line of the optical element supporting member being parallel to a center axis line of the linear power transmission member that moves in the longitudinal direction, and the optical element supporting member including a flat surface that is parallel to the axis line of the optical element supporting member, and
wherein the light reflecting body is provided on the flat surface of the optical element supporting member parallel to the axis line.

5. The optical potentiometer according to claim 2, wherein the optical element is a light transmitting body, a transmittance continuously varying along the moving direction.

6. The optical potentiometer according to claim 2, wherein the optical element is a polarizing body having a polarization property that varies continuously along the moving direction.

7. The optical potentiometer according to claim 2, wherein the linear light transmitting member includes a first linear light transmitting body configured to guide the light from the light source and output the light to the optical element, and a second linear light transmitting body configured to guide the light input from the optical element to the light receiving section.

8. The optical potentiometer according to claim 2, wherein
the optical element is supported by an optical element supporting member that is provided to be integrally movable with the linear power transmission member,
the retaining member includes a supporting member hole configured to slidably retain the optical element supporting member, and
shapes of the supporting member hole and the optical element supporting member are fitting shapes by which a relative sliding only in the longitudinal direction of the linear power transmission member to which the optical element supporting member is provided is allowed and a rotation in a circumferential direction is not allowed.

9. The optical potentiometer according to claim 2, wherein the retaining member is configured to retain the linear light transmitting member to be parallel to a moving axis line of the optical element.

10. The optical potentiometer according to claim 9, wherein the retaining member further includes an optical path changing member at an end surface of the linear light transmitting member, the optical path changing member configured to direct an optical path of the linear light transmitting member to the optical element.

11. The optical potentiometer according to claim 1, wherein
the optical element is provided on the retaining member, and
the linear light transmitting member is retained on the linear power transmission member in which the output position and the input position are provided.

12. The optical potentiometer according to claim 1, wherein
the optical element is provided at a portion of the retaining member where the linear power transmission member is retained, and
the linear light transmitting member is provided with a certain distance with respect to the optical element and so as to be integrally movable with the linear power transmission member.

13. The optical potentiometer according to claim 11, wherein the optical element is a light reflecting body, a reflectance of the light reflecting body continuously varying along the moving direction.

14. The optical potentiometer according to claim 11, wherein
the linear power transmission member at least partially includes a hollow section,
the linear light transmitting member is at least partially passed through the hollow section, and includes an optical path changing member in the hollow section, the optical path changing member being provided on an end surface of the linear light transmitting member so as to guide an optical path of the light to the optical element,
the linear power transmission member includes a light transmissive section that enables the light to pass between the optical path changing member and an external space of the linear power transmission member, and
the light transmissive section opposes the optical element.

15. The optical potentiometer according to claim 14, wherein
the linear power transmission member is configured of a hollow wire, and
the light transmissive section is configured of a hole.

16. An operating device comprising:
a tubular member having a long length and a small diameter;
a linear power transmission member configured to be inserted through the tubular member;
a moving section configured to be arranged at one end of the tubular member, one end of the linear power transmission member being fixed to the moving section, and the moving section bendably moving by a movement of the linear power transmission member in a longitudinal direction;
a driving section, the other end of the linear power transmission member being fixed to the driving section, and the driving section moving the linear power transmission member in the longitudinal direction;
the optical potentiometer according to claim 1 configured to measure an amount of displacement of the linear power transmission member; and
a computing section configured to calculate a bending angle of the moving section based on the amount of displacement of the linear power transmission member measured by the optical potentiometer.

17. The operating device according to claim 16, wherein the retaining member of the optical potentiometer is arranged at a position in the vicinity of the moving section.

18. The operating device according to claim 16, wherein the retaining member of the optical potentiometer is assembled in the moving section.

* * * * *